US008722078B2

(12) United States Patent
Gibson et al.

(10) Patent No.: US 8,722,078 B2
(45) Date of Patent: *May 13, 2014

(54) POLYMERIC DEVICE FOR CONTROLLED RELEASE OF ACTIVE AGENTS

(75) Inventors: John W. Gibson, Springville, AL (US); Arthur J. Tipton, Birmingham, AL (US)

(73) Assignee: Durect Corporation, Cupertino, CA (US)

(*) Notice: Subject to any disclaimer, the term of this patent is extended or adjusted under 35 U.S.C. 154(b) by 1211 days.

This patent is subject to a terminal disclaimer.

(21) Appl. No.: 11/888,668

(22) Filed: Jul. 31, 2007
(Under 37 CFR 1.47)

(65) Prior Publication Data
US 2009/0004273 A1    Jan. 1, 2009

Related U.S. Application Data

(63) Continuation of application No. 11/022,416, filed on Dec. 23, 2004, now abandoned.

(60) Provisional application No. 60/533,301, filed on Dec. 30, 2003, provisional application No. 60/563,377, filed on Apr. 19, 2004, provisional application No. 60/575,199, filed on May 28, 2004.

(51) Int. Cl.
*A61F 2/00* (2006.01)
*C07K 14/00* (2006.01)

(52) U.S. Cl.
USPC ............. 424/426; 514/2; 530/300; 530/350

(58) Field of Classification Search
None
See application file for complete search history.

(56) References Cited

U.S. PATENT DOCUMENTS

| | | | |
|---|---|---|---|
| 4,526,938 A | 7/1985 | Churchill et al. | |
| 4,530,840 A | 7/1985 | Tice et al. | |
| 4,622,219 A | 11/1986 | Haynes | |
| 4,725,442 A | 2/1988 | Haynes | |
| 4,745,160 A | 5/1988 | Churchill et al. | |
| 4,767,628 A | 8/1988 | Hutchinson | |
| 4,891,225 A | 1/1990 | Langer et al. | |
| 4,906,474 A | 3/1990 | Langer et al. | |
| 4,938,763 A | 7/1990 | Dunn et al. | |
| 4,942,035 A | 7/1990 | Churchill et al. | |
| 4,957,744 A | 9/1990 | Della Valle et al. | |
| 5,004,602 A | 4/1991 | Hutchinson | |
| 5,149,543 A | 9/1992 | Cohen | |
| 5,234,520 A | 8/1993 | McClintock | |
| 5,366,734 A | 11/1994 | Hutchinson | |
| 5,681,873 A * | 10/1997 | Norton et al. | 523/115 |
| 5,759,563 A | 6/1998 | Yewey et al. | |
| 6,051,558 A | 4/2000 | Burns et al. | |
| 6,159,490 A | 12/2000 | Deghenghi | |
| 6,211,152 B1 * | 4/2001 | Walsh et al. | 514/15 |
| 6,217,893 B1 | 4/2001 | Pellet et al. | |
| 6,413,536 B1 | 7/2002 | Gibson et al. | |
| 6,620,422 B1 | 9/2003 | Maquin et al. | |
| 6,630,155 B1 | 10/2003 | Chandrachekar et al. | |
| 2003/0007992 A1 * | 1/2003 | Gibson et al. | 424/426 |
| 2006/0228414 A1 | 10/2006 | Cook | |
| 2008/0176785 A1 * | 7/2008 | Brown et al. | 514/2 |
| 2008/0254086 A1 * | 10/2008 | Brown et al. | 424/422 |
| 2009/0004272 A1 * | 1/2009 | Gibson et al. | 424/486 |

FOREIGN PATENT DOCUMENTS

| | | |
|---|---|---|
| EP | 2286791 | 2/2011 |
| WO | 9808533 | 3/1998 |
| WO | 0004897 | 2/2000 |
| WO | 02/076344 | 10/2002 |
| WO | 03/000156 | 1/2003 |
| WO | 2005/067889 | 7/2005 |
| WO | 2005067889 | 7/2005 |

OTHER PUBLICATIONS

Cowar and Dunn, "Biodegradable and Nonbiodegradable Fibrous Delivery Systems", Chapter 12, pp. 145-162 (1984).*
Mylonas et al., "Preparation and evalutaion of polyanhydride microspheres containing gonadotropin-releasing hormone (GnRH), for inducing ovulation and spermiation in fish," Journal of Controlled Release, 1995, 35:23-34.
Witt et al., "The degradation, swelling and erosion properties of biodegradable implants prepared by extrusion or compression moulding of poly(lactide-co-glycolide) and ABA triblock copolymers," Biomaterials, 2000, 21:931-938.
Witt and Kissel, "Morphological characterization of microspheres, films and implants prepared from poly(lactide-co-glycolide) and ABA triblock copolymers: is the erosion controlled by degradation, swelling or diffusion?" European Journal of Pharm. and Biopharm., 2001, 51:171-181.
Youxin et al., "In-vitro degradation and bovine serum albumin release of the ABA triblock copolymers consisting of poly(L(+)lactic acid), or poly(L(+)lactic acid-co-glycolic acid) A-blocks attached to central polyoxyethylene B-blocks," Journal of Controlled Release, 1994, 32:121-128.
Zambaux et al., "Protein C-loaded monomethoxypoly (ethylene oxide)-poly(lactic acid) nanoparticles," International Journal of Pharm., 2001, 212:1-9.
Desai (1991) "Surface Modification of Polymeric Biomaterials for Reduced Thrombogenicity" *Polym. Mater. Sci. Eng.* 62:731-735.
Dunn, et al. (1985) "Fibrous Delivery Systems for Antimicrobial Agents" *Polymeric Materials in Medication* ed. C.G. Gebelein and Carraher, Plenum Publishing Corporation, pp. 47-59.
Dunn, et al. (1985) "Fibrous Polymers for the Delivery of Contraceptive Steroids to the Female Reproductive Tract" *Controlled Release of Pesticides and Pharmaceuticals* ed. D. Lewis, pp. 125-146.

(Continued)

*Primary Examiner* — Anand Desai

(57) ABSTRACT

Polymeric devices for controlled release of an active agent of interest are provided. The active agent is provided within a biodegradable polymer system to supply a polymeric device for controlled release of the active agent. The polymer system is a copolymer or a polymer blend comprising a hydrophobic component and a hydrophilic component, and the polymer system does not form a hydrogel when contacted with, or immersed in an aqueous system, for example when the device is implanted in a subject. When the device is administered to a subject, for example, when it is implanted, the device releases the active agent in a controlled fashion without a lag period, or with a minimal lag period. Methods for producing the polymeric devices are also provided, as are methods of using the polymeric devices to provide for controlled release of an active agent in a subject.

50 Claims, 3 Drawing Sheets

(56) References Cited

OTHER PUBLICATIONS

Gibson, et al. (1984) "Development of a Fibrous IUD Delivery System for Estradiol/Progesterone" *Proceedings of an Internet Workshop on Intrauterine Contraception*, Chapter 31, pp. 215-227.

Kulkarni, et al. (1966) "Polylactic Acid for Surgical Implants" *Arch. Surg.* 93(5):839-843.

Okada, et al. (1988) "One-month release injectable microcapsules of a luteinizing hormone-releasing agonist (leuprolide acetate) for treating experimental endometriosis in rats" *J. Pharmacol. Exp. Ther.* 244(2):744-750.

Penco, et al. (1998) "A New Chain Extension Reaction on Poly(lactic-Glycolic Acid) (PLGA) Thermal Oligomers Leading to High Molecular Weight PLGA-Based Polymeric Products" *Polymer International* 46(3):203-216.

* cited by examiner

Figure 1. Water uptake and swelling of mPEG-5000/(90:10 DL-PLG) at 30 °C
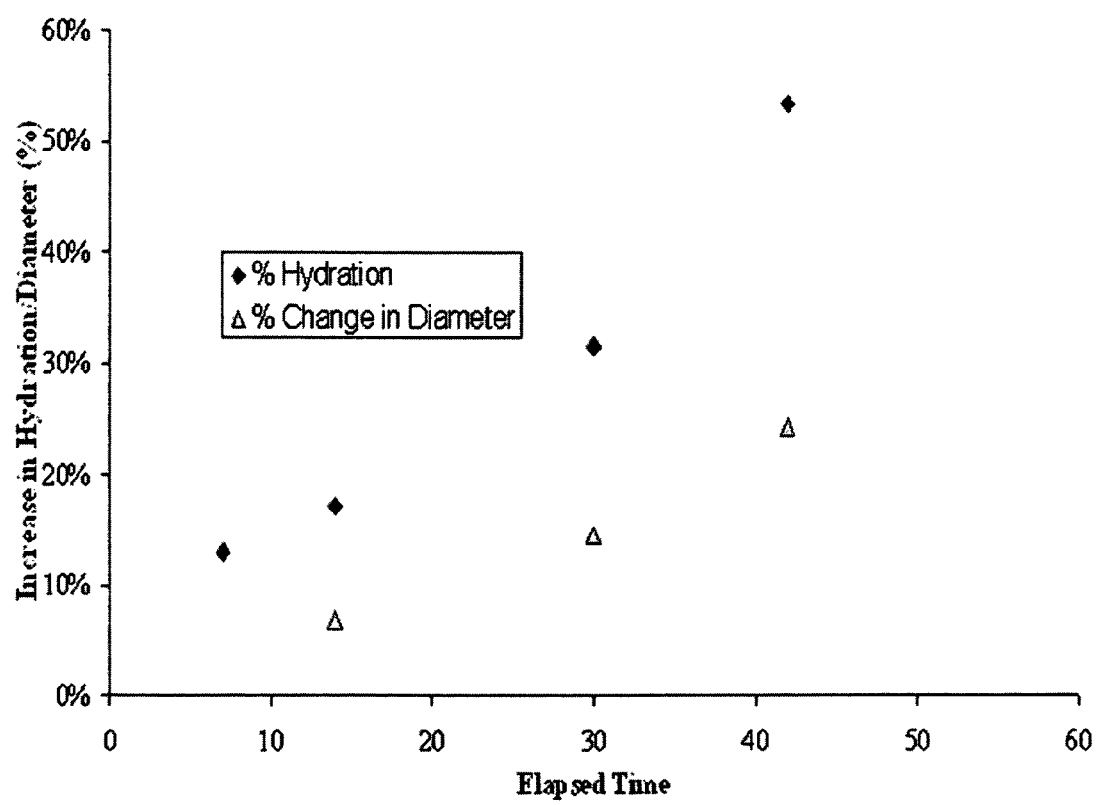

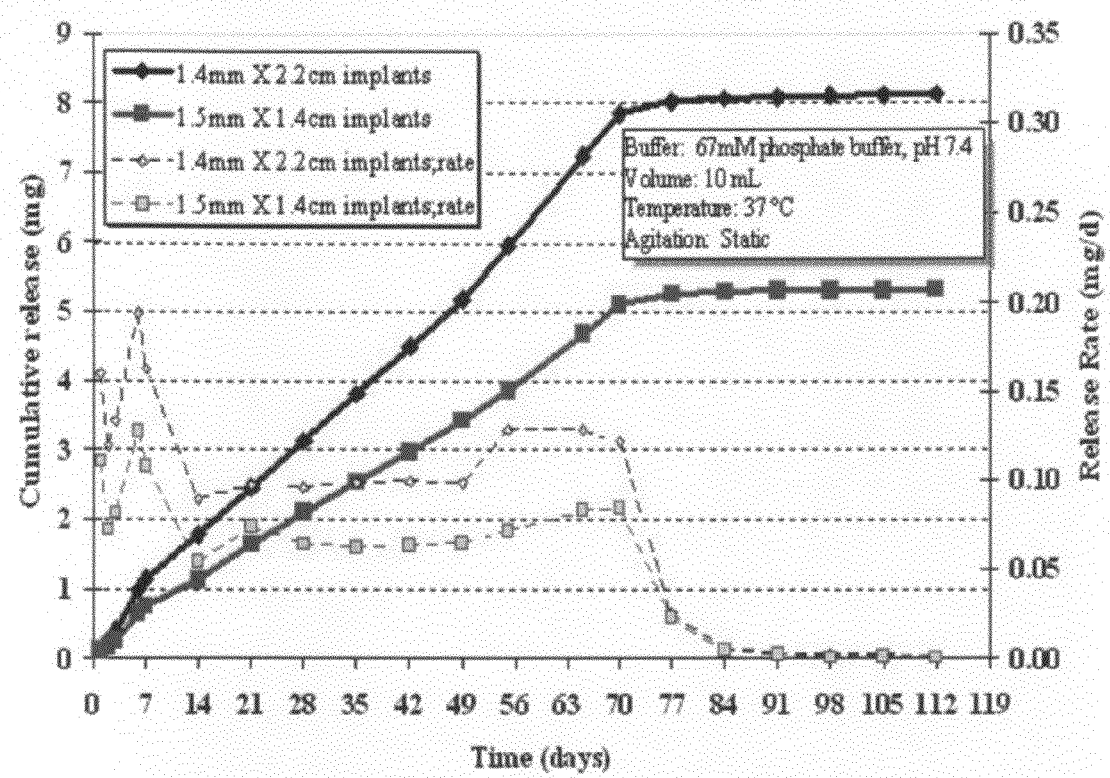
Figure 2. Effect of implant dimensions on in vitro release of leuprolide acetate from implants containing 30% wt LA in mPEG 750/(90:10 DL-PLG)

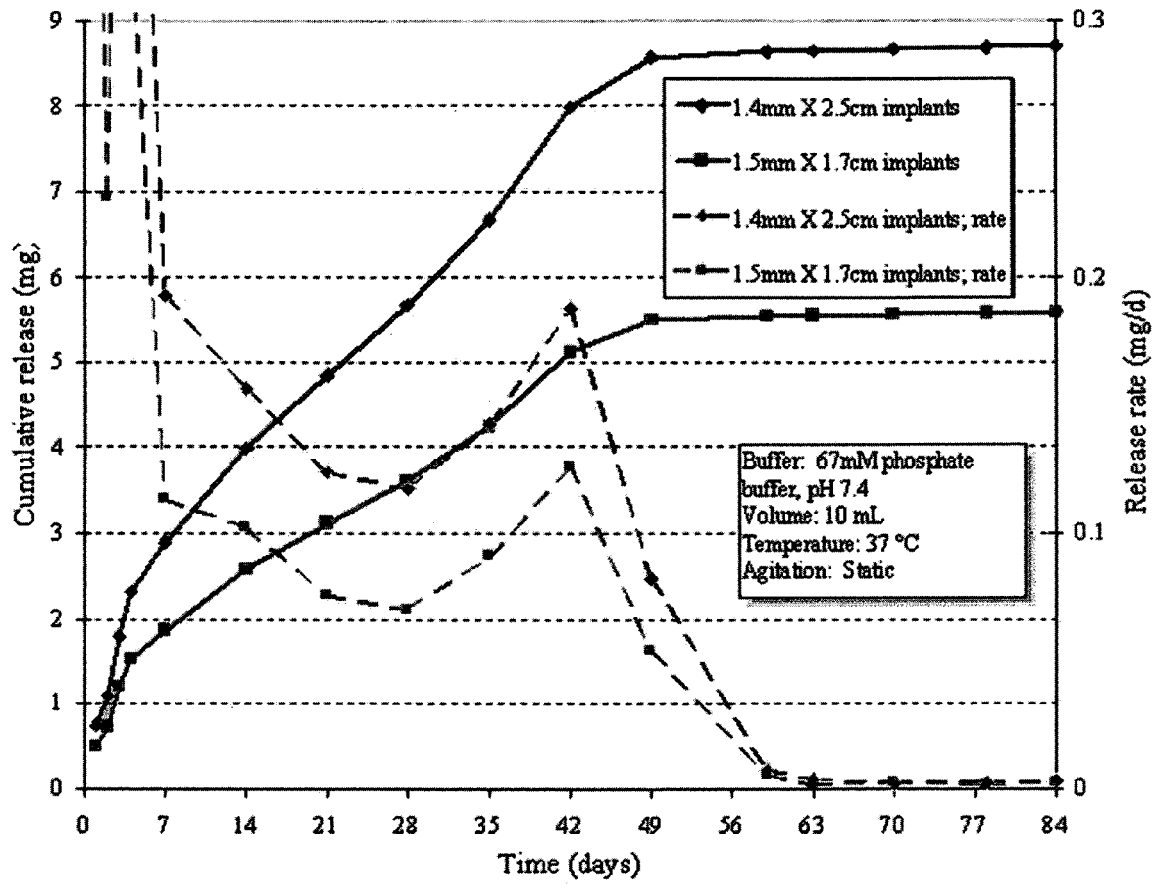
Figure 3. Effect of implant dimensions on in vitro release of leuprolide acetate from implants containing 30 wt % LA in mPEG 5K/(90:10 DL-PLG)

POLYMERIC DEVICE FOR CONTROLLED RELEASE OF ACTIVE AGENTS

This application is a continuation of co-pending U.S. application Ser. No. 11/022,416, filed on Dec. 23, 2004, herein incorporated by reference.

TECHNICAL FIELD

The present invention is generally in the field of controlled release devices for delivery of active agents such as peptide or protein biopharmaceuticals where there is a need for uniform, zero-order or linear release kinetics with minimal or no lag period.

BACKGROUND OF THE INVENTION

Biodegradable controlled release systems for active agents are well known in the art. Biodegradable matrices for drug delivery are useful because they obviate the need to remove the drug-depleted device.

The most common matrix materials used for controlled release systems are polymers. The field of biodegradable polymers has developed rapidly since the synthesis and biodegradability of polylactic acid was reported by Kulkarni et al. (1966) Arch. Surg. 93:839. Examples of other polymers which have been reported as useful as a matrix material for controlled release systems include polyanhydrides, polyesters such as polyglycolides and polylactide-co-glycolides, polyamino acids such as polylysine, polymers and copolymers of polyethylene oxide, acrylic terminated polyethylene oxide, polyamides, polyurethanes, polyorthoesters, polyacrylonitriles, and polyphosphazenes. See, e.g., U.S. Pat. Nos. 4,891,225 and 4,906,474 to Langer (polyanhydrides), 4,767,628 to Hutchinson (polylactide, polylactide-co-glycolide acid), 4,530,840 to Tice, et al. (polylactide, polyglycolide, and copolymers), and 5,234,520 (Dunn et al., biodegradable polymers for controlled delivery in treating periodontal disease).

Degradable materials of biological origin are well known including, for example, crosslinked gelatin. Hyaluronic acid has been crosslinked and used as a degradable swelling polymer for biomedical applications (see, e.g., U.S. Pat. No. 4,957,744 and Della Valle et al. (1991) Polym. Mater. Sci. Eng., 62:731-735).

Biodegradable hydrogels have also been developed for use in controlled release systems and serve as carriers of biologically active materials such as hormones, enzymes, antibiotics, antineoplastic agents, and cell suspensions. See, e.g., U.S. Pat. No. 5,149,543 to Cohen.

Hydrogel compositions are also commonly used as substrates for cell and tissue culture, impression materials for prosthetics, wound-packing materials, or as solid phase materials in size exclusion or affinity chromatography applications. For example, nonporous, deformed and/or derivatized agarose hydrogel compositions have been used in high-performance liquid chromatography and affinity chromatography methods (Li et al. (1990) Preparative Biochem. 20:107-121), and superporous agarose hydrogel beads have been used as a support in hydrophobic interaction chromatography (Gustavsson et al. (1999) J. Chromatography 830:275-284).

In the pharmaceutical fields, hydrogel monomers (natural or synthetic) are commonly added to pharmaceutical compositions (with an initiator and, sometimes, cross-linking agents) and then allowed to polymerize, thereby encapsulating a guest pharmaceutical within a hydrogel matrix. Proper choice of hydrogel macromers can produce membranes with a range of permeability, pore sizes and degradation rates suitable for a variety of applications in surgery, medical diagnosis and treatment. These techniques are used to provide microsphere carrier systems for drug targeting or controlled release systems. For example, cross-linked hydrogel microspheres have been used to encapsulate islet cells for the treatment of diabetes (Lim et al. (1980) Science 210:908-910) or cancer cells that produce cancer-suppressing materials (U.S. Pat. No. 5,888,497), and biodegradable hydrogel microspheres are widely used to encapsulate a wide variety of drug compositions, most commonly peptides and proteins (Wang et al. (1997) Pharm. Dev. and Technology 2:135-142). In these applications, the particular hydrogel system employed in the formulation is selected to provide long-term entrapment of the guest cell or pharmaceutical substance (e.g., to provide for targeted delivery or sustained- or delayed-release pharmacokinetics). Alternatively, hydrogels are employed in amphipathic copolymer systems as a hydrophilic component. In such cases the hydrogel is present in relatively large amounts such that the polymer system is capable of absorbing large amounts of water. See, e.g., U.S. Pat. Nos. 4,526,938 and 4,942,035 to Churchill et al.

SUMMARY OF THE INVENTION

Polymeric devices for controlled release of an active agent of interest are provided. The devices comprise a biodegradable polymer system selected from the group consisting of copolymers and polymeric blends comprising a hydrophobic component and a hydrophilic component combined with an active agent. The polymer system does not form a hydrogel when the device is contacted with an aqueous system.

In addition, the device releases the agent without a lag period or with a minimal lag period. In this manner, the polymeric devices of the invention provide for zero order or linear controlled release of active agents.

The active agent can be present in the devices in an amount of up to about 40 wt % or more. In certain embodiments, the active agent is a peptide therapeutic and/or prophylactic. For example, the therapeutic and/or prophylactic peptide may be selected from the group consisting of hormones, growth factors, neuroactive agents, melanotropic peptides, cell adhesion factors, cytokines, and biological response modifiers. In one preferred embodiment, the active agent is a GnRH molecule or a GNRH analogue. In certain preferred embodiments, the GnRH analog can be selected from the group consisting of desorelin, tryptorelin, goserelin, and leuprolide.

In the practice of the invention, the hydrophobic polymer component is co-polymerized with a hydrophilic polymer, or monomers, to yield a polymer system, most preferably a block copolymer, or blended with a hydrophilic polymer to yield a blended polymer system. These resultant polymer systems are characterized as having a small amount of hydrophilic character, but they will not form a hydrogel following immersion in an aqueous system. For example, preferred polymer systems for use in the compositions of the present invention may contain a water-soluble polymer such as polyethylene glycol (PEG) in amounts typically up to 25 to 30 wt %, not imparting hydrogel properties as seen with prior controlled release devices but still producing devices that exhibit monophasic or zero-order or near zero-order release kinetics. If a PEG is used in the system, the preferred molecular weight may be between about 700 Da and about 500 kDa. Other particularly preferred hydrophilic polymers for use in the polymer systems of the invention include polyvinyl pyrolidone, polyvinyl alcohols, poly (alkyleneamine)s and poly (alkyleneoxide)s.

In certain embodiments, the hydrophilic component is present in an amount of up to 25%. In other embodiments, the hydrophilic component is present in an amount of up to 15%, or present in an amount of between 0.5 and 10 weight percent. In certain other embodiments, the polymer system comprises greater than 75 wt % hydrophobic polymer.

In still further embodiments, the polymer system comprises greater than 85 wt % hydrophobic polymer, greater than 91 wt % hydrophobic polymer, or even greater than 98 wt % hydrophobic polymer.

In a preferred embodiment, the hydrophobic component of the polymer system is selected from the group consisting of polyhydroxy acids, such as poly(lactide)s, poly(glycolide)s, poly(lactide-co-glycolide)s, poly(lactic acid)s, poly(glycolic acid)s, and poly(lactic acid-co-glycolic acid)s, polyanhydrides, polyorthoesters, polyetheresters, polycaprolactone, polyesteramides, polyphosphazines, polycarbonates, polyamides, and copolymers thereof. In another preferred embodiment, the polymer system is an AB copolymer wherein the A component is a copolymer of lactide, glycolide, or caprolactone, and the B component is a polyalkyleneglycol. In a particularly preferred embodiment, the B component is a polyalkyleneglycol at 1.25 weight percent and the hydrophobic polymer is poly(lactide-co-glycolide).

In any of the devices of the present invention, the active agent can be distributed uniformly within the polymer. The devices may be formed wherein the active agent is incorporated into the polymer system using a non-solvent process. Additionally, the devices may be formed by dry melt extrusion, or melt extrusion of a copolymer. In one preferred embodiment, the device is made with a double extrusion step, to insure maximum dispersion of the active agent in the polymer, without the use of solvent. The hydrophilic component of the polymer is present in an amount facilitating uptake of water, but less than that which would result in the formation of a hydrogel, typically less than 25 wt % of the polymer. The active agent is typically incorporated in an amount of up to 40 wt %, although it can be higher, preferably in the case of peptides.

The devices of the present invention can be provided in any suitable form depending upon the manner in which the device will be administered. In this regard, the present devices may be administered by oral routes (e.g., as capsules such as hard capsules and soft capsules, solid preparations such as granules, tablets, pills, troches or lozenges, cachets, pellets, powders, particulates, microparticulates (and any other particulate form) and non-oral routes (e.g., as intramuscular, subcutaneous, transdermal, visceral, IV (intravenous), IP (intraperitoneal), intraarterial, intrathecal, intracapsular, intraorbital, intraocular, intratumoral, perivascular, intracranial, periophthalmic, inside the eyelid, intranasal, intrasinus, intrabladder, intravaginal, intraurethral, intrarectal, adventitial, injectable, pulmonary, inhalable, transmucosal, and other suitable forms).

In preferred embodiments, the devices are administered by implantation, and are thus configured as a shaped article, such as a sphere, rod, slab, film, fiber, needle, cylinder, sheet, tube, or any other suitable geometry including microparticles, microspheres, and/or microcapsules. The devices can be provided in any suitable size and shape of implantable device for specialized locations, for example as a catheter, shunt, device for continuous subarachnoid infusion, feeding tube, solid implant to prevent surgical adhesion, uterine implant, artificial sphincter, periurethral implant, splint, opthlamic implant, contact lens, plastic surgery implant, stent (containing or coated with the active agent) including an esophageal stent, gastrointestinal stent, vascular stent, biliary stent, colonic stent, pancreatic stent, ureteric stent, urethral stent, lacrimal stent, Eustachian tube stent, fallopian stent, nasal stent, sinus stent, tracheal stent, or bronchial stent, or a port including a venous access device, implanted port, epidural catheter or central catheter (PICC).

The devices can be implanted at a desired site surgically, or using minimally invasive techniques employing trocars, catherers, etc. Such implants can thus be implanted into any suitable tissue using standard techniques, such as implanted intradermally, subdermally, subcutaneously, intraperitoneally, intramuscularly, or intralumenally (e.g., intraarterially, intravenously, intravaginally, rectally, or into the periodontal space). The devices can alternatively be fabricated as part of a matrix, graft, prosthetic or coating. If an implantable device is manufactured in particulate form, e.g., as a microparticle, microsphere or microcapsule, it can then be implanted into suitable tissue using a cannula, needle and syringe or like instrument to inject a suspension of the particles.

In the methods of the invention, the devices can be administered using any suitable procedure. Depending upon the active agent to be administered, the selected form (size, shape, etc.) and the selected site of administration, the devices can be delivered or implanted using minimally invasive procedures at a site where release is desired. These procedures can include implantation using trocars or catheters, injection using standard needle and syringes (of, e.g., powders, particles, microparticles, microspheres, microcapsules), ingrafting or surgical or non-surgical placement (of, e.g., a matrix, graft, prosthetic or coating), inhalation (of, e.g., powders or particulates), and the like. The devices are designed so that the active agent is released in the desired dosage over a defined period of time. The devices are designed so that they degrade during and after release of the active agent is achieved.

In one preferred method, the device is formulated to include a GNRH molecule or GnRH analogue in a solid implant form. The device is then administered to a subject in order achieve a certain target blood level, production, function, or activity of a gonadotrophin (LH or FSH) in the subject.

BRIEF DESCRIPTION OF THE DRAWINGS

FIG. 1 is a graph of water uptake and swelling of mPEG-5000-DL-PLG, (90:10) at 37° C., measured as increase in hydration over time.

FIG. 2 is a graph of cumulative release and rate of release of peptide over time (days) from various sized devices prepared with 30 weight percent (wt %) leuprolide acetate in mPEG-750 ☐L-PLG 90:10 block copolymer.

FIG. 3 is a graph of the effect of device dimensions on in vitro release of leuprolide acetate ("LA") from devices containing 30 wt % LA in mPEG 5K DL-PLG (90:10) block copolymer.

DETAILED DESCRIPTION OF THE PREFERRED EMBODIMENTS

Before describing the present invention in detail, it is to be understood that this invention is not limited to particularly exemplified polymer systems or process parameters as such may, of course, vary. It is also to be understood that the terminology used herein is for the purpose of describing particular embodiments of the invention only, and is not intended to be limiting.

All publications, patents and patent applications cited herein, whether supra or infra, are hereby incorporated by reference in their entirety.

It must be noted that, as used in this specification and the appended claims, the singular forms "a," "an" and "the" include plural referents unless the content clearly dictates otherwise. Thus, for example, reference to "a hydrorphobic polymer" includes a mixture of two or more such polymers, reference to "an agent" or "an active agent" includes mixtures of two or more such agents, and the like.

It is an object of the present invention to provide a controlled release device which is biodegradable, that releases an active agent such as a drug over a prolonged period of time, and that provides more controlled zero-order or linear release kinetics rather than biphasic release kinetics.

It is a further object of the present invention to provide a method of making such devices that is cost-effective, highly reproducible, and efficient, and utilizes minimal if any solvent.

Compositions and methods that enable a more constant or linear rate of release of active agents such as peptide or protein drugs from monolithic compositions prepared with a hydrolytically biodegradable hydrophobic polymer such as poly (DL-lactide-co-glycolide), DL-PLG, have been developed which incorporates a small amount of hydrophilic polymer into the device. The use of hydrophobic polymers such as PLGs with incorporation of small amounts of hydrophilic polymer such as poly (ethylene glycol), PEG, preferably covalently linked into the hydrophobic polymer backbone provides particularly beneficial release profiles. In addition, the combination of such material choices with a simple process involving for example dry blending, compounding (first-pass extrusion), grinding, and re-extrusion can further provide for beneficial release profiles. The monolithic compositions or device can be any shaped article such as a sphere, cylinder, sheet, or other geometry including microparticles, microspheres, and/or microcapsules comprising a mixture of a drug such as peptide and a hydrophobic polymer incorporating a small amount of hydrophilic polymer, either in the form of a copolymer or a blend. A preferred manufacturing process avoids the use of solvent to mix polymer and drug.

The device is designed to provide monophasic release, i.e., where release is typically linear or zero order, but may include continuous release where the initial "burst" or "lag" effect is minimal or not present.

There are a number of problems facing the skilled artisan associated with the long-term delivery of biologically active polypeptides such as polypeptide hormones from biodegradable, implantable delivery systems. Because peptides are generally not soluble in hydrophobic polymers such as DL-poly-lactide-co-glycolide ("DL-PLG"), solid compositions comprising a mixture of peptide and DL-PLG are typically provided as two-phase compositions in which the minor component (e.g. the peptide) exists as a dispersed phase within the major component (e.g. the DL-PLG). In addition, because of the glassy nature of the DL-PLGs, these materials are generally not very permeable to molecules the size of peptides, especially those that are water-soluble. As a result, the release of peptides from DL-PLGs typically does not occur by simple diffusion through the polymer matrix. Rather, release occurs by diffusion through aqueous channels that form when the solid composition is placed into an aqueous environment.

When a prior art polymeric composition is placed into an aqueous environment, water is absorbed and dissolves the dispersed peptide, resulting in domains of a concentrated aqueous solution of the peptide dispersed within the polymer matrix. The peptide that is in contact with the surface of the formulation is released by diffusion through the aqueous channels formed by hydration of the polymer. This occurs almost instantaneously as the diffusion path and resistance are low. At relatively low loadings of peptide in the DL-PLG matrix, however, release ceases or slows dramatically once the surface-associated peptide is depleted, because peptide that is remote from the surface has no pathway through which it can diffuse to the surface. Then as degradation proceeds, the increase in hydroxyl and carboxylic acid end groups results in a gradual increase in the hydrophilicity of the matrix. As the water content of the matrix increases, new aqueous channels form, providing pathways through which the more remote peptide can diffuse to the surface and be released. The resulting release profile tends to be biphasic in which two periods of release are separated by a period during which little or no peptide release occurs. The "dead" period that occurs between the two release phases is particularly problematic for many peptides such as gonadotrophin releasing hormone ("GnRH") agonists where the objective is continuous suppression of the gonadotrophic hormone such as leutinizing hormone ("LH").

One approach to minimize or eliminate the "dead" period involves increasing the peptide content of the composition. As the peptide content of the composition is increased, interparticle contact between the peptide particles increases, providing a more extensive network of pores, and the proportion of peptide that is released during the initial phase increases, ultimately comprising most if not all of the drug in the composition. Release typically follows the well-known Higuchi model for release from a dispersed-drug monolithic device and exhibits square-root-of-time kinetics.

Another approach to minimizing the dead period and achieving a more constant release of drug involves the use of polymer compositions that degrade relatively rapidly. For example, U.S. Pat. Nos. 4,767,628, 5,004,602, 5,366,734 to Hutchinson describe continuous release compositions in which the initial diffusion-controlled phase of release and the second degradation-controlled phase of release are made to overlap by careful choice of the monomer ratio and the molecular weight of the DL-PLG. The art describes blending two or more excipients of different monomer composition and molecular weight to achieve the desired release profile. The method of producing such implant systems involves solvent blending the peptide and the excipient(s) in glacial acetic acid, freeze-drying the mixture to remove the acetic acid, and molding or extruding the freeze-dried composition to form the implant.

Still another approach involves the use of biodegradable hydrogels so that the permeability of the peptide in the polymer matrix is significantly increased. For example, U.S. Pat. Nos. 4,526,938 and 4,942,035 to Churchill describe continuous release compositions comprising a pharmacologically active peptide and an amphipathic block copolymer in which the hydrophobic component is biodegradable and the hydrophilic component may or may not be biodegradable. Generally, these compositions contain relatively large amounts of the hydrophilic component such that the resulting polymers are hydrogels capable of absorbing large amounts of water. For example, a polymer containing 25 parts of PEG and 75 parts of poly (DL-lactide) having an inherent viscosity of 0.41 dL/g when pressed into a thin film of 0.2 mm, takes up its own weight in water over 24 hours at 37° C. Churchill et al. describe implants prepared from the same polymer composition as well as implants prepared from a block copolymer comprising 5 wt % PEG-6000 and 95 wt % of DL-PL. The implants contain 23.8 wt % goserelin acetate. Goserelin was released continuously in vitro from these systems for approximately 18 days from the more hydrophilic and for more than 250 days from the less hydrophilic implants. These compositions are also prepared by solvent blending the peptide and polymer using glacial acetic acid, followed by lyophilization.

U.S. Pat. No. 6,159,490 to Deghenghi describes a method for producing implants for delivery of peptides from copolymers of lactide and glycolide for periods of from 1 to 12 months. Deghenghi's process involves first producing an intimate mixture of the peptide and polymer by: (1) grinding the polymer; (2) combining the ground polymer with an aqueous slurry of the peptide; and (3) drying the mixture to remove the water. Afterwards, the mixture is melt extruded at 70 to 110° C. U.S. Pat. No. 6,217,893 to Pellet et al. describes compositions providing continuous release of peptides from polymers or copolymers of lactide and glycolide having inherent viscosities of between 0.5 and 1.6 dL/g in $CHCl_3$ and a hydrophilic character. Hydrophilic character is defined as a polymer having polar chain ends and further defined as those having an acid number of 1 or greater and preferably of 1.5 to 2. Pellet also describes the need for a peptide of high specific surface area. No examples of the preparation of or release from implants are given.

The method described by Hutchinson and Churchill utilizes polymer and drug blending using glacial acetic acid as a solvent. An alternative aqueous process is described in U.S. Pat. No. 6,159,490 to Deghenghi for producing implants for delivery of peptides from copolymers of lactide and glycolide for periods of from 1 to 12 months. Deghenghi's process involves first producing an intimate mixture of the peptide and polymer by: (1) grinding the polymer; (2) combining the ground polymer with an aqueous slurry of the peptide; and (3) drying the mixture to remove the water. Afterwards, the mixture is melt extruded at 70 to 110° C.

These past approaches to eliminate the "dead" period for release involve approaches that either require a mix of two different polymers, require a polymer that swells to form a hydrogel, or require a polymer with an increased number of endgroups with acidic function or other hydrophilic end group. The mix of two polymers requires inventorying and performing all steps with two materials as well as providing for an additional process step in manufacture. PLGs with the addition of enough PEG to form hydrogels after placement in an aqueous environment will swell to a large extent, and may not be homogeneous. Polymers with a higher amount of acidic endgroups can only be varied over a narrow range, as there are typically only one acidic end group per molecule, and an alcohol function that is uniformly present. In terms of the process for manufacture, all of the above examples involve some type of solvent blending using either an organic solvent or water. This creates the potential for solvent residues that may have an adverse effect on the polymer or subject. In addition the solvent mixing step may create the potential for drug or polymer degradation, and has time and cost consequences for scale up.

These same considerations apply to non-peptide agents as well.

I. Materials and Compositions

A. Polymer Systems

The processes disclosed herein can be used to form devices from a variety of biocompatible and biodegradable polymers. Biodegradable, as defined herein, means the polymer will degrade or erode in vivo to form smaller chemical species, wherein the degradation can result, for example, from enzymatic, chemical, and physical processes. In the most preferred embodiment, the polymer is substantially hydrophobic and degrades by hydrolysis. The term "biocompatible" is used herein to refer to a polymer and any degradation products of the polymer that present no significant, deleterious or untoward effects on the recipient's body.

Examples of biodegradable polymers and oligomers suitable for use in the compositions and methods of the present invention include, but are not limited to: poly(lactide)s; poly(glycolide)s; poly(lactide-co-glycolide)s; poly(lactic acid)s; poly(glycolic acid)s; and poly(lactic acid-co-glycolic acid)s; poly(caprolactone)s; poly(malic acid)s; polyamides; polyanhydrides; polyamino acids; polyorthoesters; polyetheresters; polycyanoacrylates; polyphosphazines; polyphosphoesters; polyesteramides; polydioxanones; polyacetals; polyketals; polycarbonates; polyorthocarbonates; degradable polyurethanes; polyhydroxybutyrates; polyhydroxyvalerates; polyalkylene oxalates; polyalkylene succinates; chitins; chitosans; oxidized celluloses; and copolymers, terpolymers, blends, combinations or mixtures of any of the above materials.

As used herein, "hydrophobic" refers to a polymer that is substantially not soluble in water. As used herein, "hydrophilic" refers to a polymer that may be water-soluble or to a polymer having affinity for absorbing water, but typically not when covalently linked to the hydrophobic component as a co-polymer, and which attracts water into the device.

Hydrophilic polymers suitable for use herein can be obtained from various commercial, natural or synthetic sources well known in the art. Suitable hydrophilic polymers include, but are not limited to: polyanions including anionic polysaccharides such as alginate; agarose; heparin; polyacrylic acid salts; polymethacrylic acid salts; ethylene maleic anhydride copolymer (half ester); carboxymethyl amylose; carboxymethyl cellulose; carboxymethyl dextran; carboxymethyl starch; carboxymethyl chitin/chitosan; carboxy cellulose; 2,3-dicarboxycellulose; tricarboxycellulose; carboxy gum arabic; carboxy carrageenan; carboxy pectin; carboxy tragacanth gum; carboxy xanthan gum; carboxy guar gum; carboxy starch; pentosan polysulfate; curdlan; inositol hexasulfate; beta.-cyclodextrin sulfate; hyaluronic acid; chondroitin-6-sulfate; dermatan sulfate; dextran sulfate; heparin sulfate; carrageenan; polygalacturonate; polyphosphate; polyaldehydro-carbonic acid; poly-1-hydroxy-1-sulfonate-propen-2; copolystyrene maleic acid; mesoglycan; sulfopropylated polyvinyl alcohols; cellulose sulfate; protamine sulfate; phospho guar gum; polyglutamic acid; polyaspartic acid; polyamino acids; and any derivatives or combinations thereof. One skilled in the art will appreciate other hydrophilic polymers that are also within the scope of the present invention.

Various water-soluble polymers suitable for use herein include, but are not limited to: poly (alkyleneglycol), polyethylene glycol ("PEG"); propylene glycol; ethylene glycol/propylene glycol copolymers; carboxylmethylcellulose; dextran; polyvinyl alcohol ("PVOH"); polyvinyl pyrolidone; poly (alkyleneamine)s; poly (alkyleneoxide)s; poly-1,3-dioxolane; poly-1,3,6-trioxane; ethylene/maleic anhydride copolymers; polyaminoacids; poly (n-vinyl pyrolidone); polypropylene oxide/ethylene oxide copolymers; polyoxyethylated polyols; polyvinyl alcohol succinate; glycerine; ethylene oxides; propylene oxides; poloxamers; alkoxylated copolymers; water soluble polyanions; and any derivatives or combinations thereof. In addition, the water-soluble polymer may be of any suitable molecular weight, and may be branched or unbranched.

In the practice of the invention, the hydrophobic polymer component is co-polymerized with a hydrophilic polymer, or monomers, to yield a polymer system, most preferably a block copolymer, or blended with a hydrophilic polymer to yield a blended polymer system. These resultant polymer systems are characterized as having a small amount of hydrophilic character, but they will not form a hydrogel following immersion in an aqueous system. For example, preferred polymer systems for use in the compositions of the present invention may contain a water-soluble polymer such as polyethylene glycol (PEG) in amounts typically up to 25 to 30 wt %, not imparting the hydrogel properties cited by Churchill but producing devices that exhibit monophasic or zero-order or near zero-order release kinetics. If a PEG is used in the system, the preferred molecular weight may be between about 700 Da and about 500 kDa. Other particularly preferred hydrophilic polymers for use in the polymer systems of the invention include polyvinyl pyrolidone, polyvinyl alcohols, poly (alkyleneamine)s and poly (alkyleneoxide)s.

As used herein, "polymer" and "polymer system" include copolymers and blends unless otherwise expressly defined. The polymer systems can be produced using standard copolymerization techniques, such as graft copolymerisation, polycondensation and polyaddition, optionally with an appropriate catalyst. These techniques can be carried out in conventional manner well known in the polymer art as regards to time and temperature. Alternatively, the polymer systems can be produced using standard blending techniques of polymers or blending of copolymers, again carried out in conventional manner well known in the polymer art as regards to time and temperature.

The polymer system, method of manufacture, and drug loading are selected such that the device does not form a hydrogel when contacted with or immersed in an aqueous system, for example, when implanted in vivo into an animal or human subject. The polymer system is characterized by a reduced hydrophobicity relative to the pure hydrophobic polymer component by virtue of the inclusion of the hydrophilic component. This facilitates uptake of water by the device and dissolution and release of the incorporated active agent or agents, avoiding a lag period and leading to linear or near zero order release kinetics.

As used herein, the term "hydrogel" is used in its usual manner within the art, for example to refer to a polymer or polymer system that swells in the presence of water or other aqueous system, shrinks in the absence or reduction of the amount of water, is able to retain a significant fraction of water within its structure, and typically does not dissolve in water. One skilled in the art will appreciate that there are a number of standard tests that one can employ in order to determine if a polymer or polymer system will act as a hydrogel, e.g., form a hydrogel, when immersed in an aqueous system such as when it is implanted in vivo into an animal or human subject.

For example, a polymer or polymer system can be prepared in particulate form, or comminuted or rendered into particles to form a powder. The powder can then be mixed with distilled water in a suitable container and allowed sufficient time to form a gel, for example from about 15 minutes to 24 hours or more. The resultant solution can then be viewed using standard optical microscopy to look for the formation of a characteristic gel-like suspension and thereby determine that a hydrogel has formed, or to see if the particles have failed to form a suspension and/or precipitated out of the solution, indicating that the polymer system does not form a hydrogel when immersed in an aqueous system.

Alternatively, or in addition to the above-noted procedure, the absorbency of the polymer or polymer system in an aqueous system can be assessed, wherein the ability of a polymer to absorb water is a characteristic feature of a hydrogel-forming polymer. The term "absorbency" as used herein can thus mean a value determined according to the following procedure. In the case of deionized water-absorbency, 2 liters of deionized water and 1 g of the dried polymer can be placed in a 3-liter beaker, and water allowed to be absorbed by the polymer for from about 30 minutes to 24 hours or more with stirring, after which the polymer is collected by filtration with a 100-mesh metallic wire gauze, the volume of the swollen polymer obtained as a filtered cake can then be measured by means of a messcylinder. The value thus taken can then be used as the deionized water-absorbency value of the polymer. A higher absorbency value, such as a value up to the starting weight of the polymer, indicates that a hydrogel was formed, whereas low values indicate that no hydrogel was formed.

In the case of saline solution-absorbency, 200-ml of saline solution (0.9% by weight aqueous sodium chloride solution) and 1 g of dried polymer can be placed in a 300-ml beaker and the polymer allowed to absorb the solution for from about 30 minutes to about 24 hours or more with stirring, after which it is filtered with a 200-mesh metallic wire gauze, the volume of the swollen polymer obtained as a filtered cake can be measured by means of a messcylinder. The value obtained can then be used as the saline solution-absorbency value of the polymer. Here again, high values, such as those approaching or exceeding the starting weight of the polymer, indicate the formation of a hydrogel.

In another test, referred to as a centrifuge retention capacity test, a small amount of the polymer can be weighed into a teabag that is subsequently welded shut. The teabag is then placed in an excess of 0.9% by weight sodium chloride solution (at least 1.25 to 1 of sodium chloride solution/1 g of the suspected hydrogel). After a swelling time of about 20 minutes to about 24 hours or more, the teabag is removed from the sodium chloride solution and centrifuged at 250 g for three minutes. The centrifuged teabag can then be weighed to determine the amount of liquid retained by the hydrogel. Retention of any significant amount of liquid by the test composition indicates that a hydrogel was formed.

In addition to the above-described assessments, there are numerous other tests readily available to the skilled artisan whereby the ability of a selected polymer or polymer system to form a hydrogel when immersed in an aqueous system can be determined.

B. Active Agents

Essentially any active agent can be incorporated with the polymer system to form a device according to the present invention using conventional processes including those methods described herein. Accordingly, as used herein an "active agent" can include any compound or composition of matter which, when administered to an organism (human or animal subject) induces a desired pharmacologic and/or physiologic effect by local and/or systemic action. The term therefore encompasses those compounds or chemicals traditionally regarded as drugs, biopharmaceuticals (including molecules such as peptides, proteins, nucleic acids), and vaccines. The term further encompasses those compounds or chemicals traditionally regarded as diagnostic agents.

Active agents useful in the practice of the present invention thus include compounds or compositions acting at synaptic and neuroeffector junctional sites (cholinergic agonists, anticholinesterase agents, atropine, scopolamine, and related antimuscarinic drugs, catecholamines and sympathomimetic drugs, and adrenergic receptor antagonists); drugs acting on the central nervous systems; autacoids (drug therapy of inflammation); drugs affecting renal function and electrolyte metabolism; cardiovascular drugs; drugs affecting gastrointestinal function; chemotherapy of neoplastic diseases;

drugs acting on the blood and the blood-forming organs; and hormones and hormone antagonists. As used herein, the term "drug" includes any substance intended for use in the cure, mitigation, treatment, or prevention of any disease, disorder, or condition or intended to affect the structure or function of the body, other than food. The term can include any beneficial agent or substance that is biologically active or meant to alter animal physiology. Drugs may be natural or synthetic organic compounds, proteins, peptides, nucleic acid molecules, glycoproteins, sugars, carbohydrates, lipids, or combinations thereof. Peptides and proteins are particularly preferred drugs for use in the compositions of the present invention.

More specifically, classes of active agents useful in the present compositions include, but are not limited to, anti-infectives such as antibiotics and antiviral agents; analgesics and analgesic combinations; local and general anesthetics; anorexics; antiarthritics; antiasthmtic agents; anticonvulsants; antidepressants; antihistamines; anti-inflammatory agents; antinauseants; antimigrane agents; antineoplastics; antipruritics; antipsychotics; antipyretics; antispasmodics; cardiovascular preparations (including calcium channel blockers, beta-blockers, beta-agonists and antiarrythmics); antihypertensives; diuretics; vasodilators; central nervous system stimulants; cough and cold preparations; decongestants; diagnostics; hormones; bone growth stimulants and bone resorptioninhibitors; immunosuppressives; muscle relaxants; psychostimulants; sedatives; tranquilizers; proteins, peptides, and fragments thereof; and nucleic acid molecules (polymeric forms of two or more nucleotides, either ribonucleotides (RNA) or deoxyribonucleotides (DNA) including double- and single-stranded molecules and supercoiled or condensed molecules, gene constructs, expression vectors, plasmids, antisense molecules and the like.

One class of drugs of particular interest for use herein as an active agent is the class of anesthetics, such as benzocaine, bupivacaine, etidocaine, lidocaine, mepivacaine, pramoxine, prilocalne, procaine, proparacaine, ropivacaine, tetracaine, levobupivacaine, chloroprocaine, butacaine, propoxycaine, phenacaine, hexylcaine, isobucaine, cyclomethycaine, benoxinate, diperodon, dibucaine, meprylcaine, dimethisoquin, pramoxine, butamben, dyclonine (with and without augmenting agents such as dexamethasone or epinephrine).

Another class of drug of particular interest for use as an active agent herein is the opioids class, which includes alfentanil, allylprodine, alphaprodine, anileridine, apomorphine, apocodeine, benzylmorphine, bezitramide, buprenorphine, butorphanol, clonitazene, codeine, cyclazocine, cyclorphen, cyprenorphine, desomorphine, dextromoramide, dezocine, diampromide, dihydrocodeine, dihydromorphine, dimenoxadol, dimepheptanol, dimethylthiambutene, dioxyaphetyl butyrate, dipipanone, eptazocine, ethoheptazine, ethylmethylthiambutene, ethylmorphine, etonitazene, fentanyl, heroin, hydrocodone, hydroxymethylmorphinan, hydromorphone, hydroxypethidine, isomethadone, ketobemidone, levallorphan, levorphanol, levophenacylmorphan, lofentanil, meperidine, meptazinol, metazocine, methadone, methylmorphine, metopon, morphine, myrophine, nalbuphine, narceine, nicomorphine, norlevorphanol, normethadone, nalorphine, normorphine, norpipanone, ohmefentanyl, opium, oxycodone, oxymorphone, papavereturn, pentazocine, phenadoxone, phenomorphan, phenazocine, phenoperidine, pholcodine, piminodine, piritramide, propheptazine, promedol, profadol, properidine, propiram, propoxyphene, remifentanyl, sufentanyl, tramadol, tilidine, naltrexone, naloxone, nalmefene, methylnaltrexone, naloxone methiodide, nalorphine, naloxonazine, nalide, nalmexone, nalbuphine, nalorphine dinicotinate, naltrindole (NTI), naltrindole isothiocyanate, (NTII), naltriben (NTB), nor-binaltorphimine (nor-BNI), beta-funaltrexamine (b-FNA), BNTX, cyprodime, ICI-174,864, LY117413, MR2266, etorphine, DAMGO, CTOP, diprenorphine, naloxone benzoylhydrazone, bremazocine, ethylketocyclazocine, U50,488, U69,593, spiradoline, DPDPE, [D-Ala2,Glu4] deltorphin, DSLET, Met-enkephalin, Leu-enkephalin, β-endorphin, dynorphin A, dynorphin B, a-neoendorphin, or an opioid having the same pentacyclic nucleus as nalmefene, naltrexone, buprenorphine, levorphanol, meptazinol, pentazocine, dezocine, or their pharmacologically effective esters or salts.

Still another class of drugs of particular interest for use herein as an active agent is the class of non-steroidal antinflammatory drugs ("NSAIDs") which includes salicylates, pyrazolons, indomethacin, sulindac, the fenamates, tolmetin, and propionic acid derivatives; for example, salicylic acid, aspirin, methyl salicylate, diflunisal, salsalate, phenylbutazone, indomethacin, oxyphenbutazone, apazone, mefenamic acid, meclofenamate sodium, ibuprofen, naproxen, naproxen sodium, fenoprofen, ketoprofen, flurbiprofen, piroxicam, diclofenac, etodolac, ketorolac, aceclofenac, nabumetone, and the like.

Proteins are yet an even further preferred class of drugs for use as the active agent in the practice of the present invention. The term "protein" includes peptides, polypeptides, consensus molecules, analogs, derivatives or combinations thereof. The term thus encompasses recombinant or naturally occurring molecules, whether human or animal in origin, including naturally occurring, synthetic, semi-synthetic or recombinantly produced. Examples of suitable peptide and/or protein active agents for use in the present compositions include hormones, growth factors, neuroactive agents, hematopoietic factors, melanotropic peptides, cell adhesion factors, cytokines and biological response modifiers, anti-obesity factors, trophic factors, anti-inflammatory factors, enzymes and antibody molecules. Preferred cytokines and biological response modifiers include interferons (see, e.g., U.S. Pat. Nos. 5,372,808; 5,541,293; 4,897,471; and 4,695,623) and interleukins (see, e.g., U.S. Pat. No. 5,075,222). Preferred hematopoietic factors include erythropoietins (see, e.g., U.S. Pat. Nos. 4,703,008; 5,441,868; 5,618,698; 5,547,933; and 5,621,080) and preferred anti-obesity factors include the OB protein (see, e.g., International Publication Nos. WO 96/40912; WO 96/05309; WO 97/00128; WO 97/01010 and WO 97/06816). Preferred growth factors include granulocyte-colony stimulating factors (see, e.g., U.S. Pat. Nos. 4,999,291; 5,581,476; 5,582,823; 4,810,643 and International Publication No. WO 94/17185); stem cell factor (see, e.g., International Publication Nos. WO 91/05795; WO 92/17505 and WO 95/17206); bovine and human forms of basic fibroblast growth factor including analogs thereof (see, e.g., U.S. Pat. Nos. 5,859,208; 5,604,293; 5,514,566; 5,439,616; 5,464,774; 5,155,214; and 4,956,455); and bovine and human forms of vascular endothelial growth factor including analogs thereof (see, e.g., Ferrara et al. (1991) *J. Cellular Biochem.* 47:211-218; Connolly (1991) *J. Cellular Biochem.* 47:219-223; Joukov et al. (1996) *EMBO J.* 15:290-298, and International Publication Nos. WO 96/26736 and WO 95/24473).

A particularly preferred hormone for use as an active agent is gonadotropin releasing hormone ("GnRH"), also known as luteinizing hormone releasing hormone ("LHRH"), and analogs thereof. GnRH is of central importance to the regulation of fertility. Johnson et al. (1988) *Essential Reproduction*, 3rd Edn. Blackwell Scientific Publications. In males and females, GnRH is released from the hypothalamus into the bloodstream and travels via the blood to the pituitary, where it induces the release of the gonadotropins, luteinizing hormone ("LH") and follicle stimulating hormone ("FSH") by gonadotroph cells, and regulates androgens, estrogens, and progestins.

As used herein, the term "GnRH analogue" is intended to encompass peptidic compounds that mimic the structure of luteinizing hormone releasing hormone. A GnRH analogue may be a GnRH agonist or a GNRH antagonist.

As used herein, a "GNRH agonist" is intended to refer to a compound that stimulates the GNRH receptor such that release of luteinizing hormone and/or FSH is stimulated. Examples of GnRH agonists include leuprolide (trade name: Lupron®, Abbott/TAP; Viadur®, Alza), goserelin (trade name: Zoladex®; Zeneca), buserelin (Hoechst), triptorelin (also known as Decapeptyl, D-Trp-6-LHRH and Debiopharm®; Ipsen/Beaufour), nafarelin (trade name Synarel®; Syntex), lutrelin (Wyeth), cystorelin (Hoechst), gonadorelin (Ayerst) and histrelin (Ortho), luliberin, desorelin, avorelin, cetrrelix, teverelix, ramorelix, ganirelix, antide, nictide, and azaline. Leuprolide agonists are particularly preferred for use in the compositions of the present invention.

As used herein, the term "GnRH antagonist" is intended to refer to a compound that inhibits the GnRH receptor such that release of luteinizing hormone or FSH is inhibited. Examples of GnRH antagonists include Antide, Cetrorelix, Ganirelix, and compounds described in U.S. Pat. Nos. 5,470,947; 5,413,990; 5,371,070; 5,300,492; 5,296,468; 5,171,835; 5,003,011; 4,992,421; 4,851,385; 4,801,577; 4,689,396; and 4,431,635, and International Publication No. WO 89/01944.

In addition, other protein active agents for use herein include, but are not limited to, anti-obesity related products, insulin, gastrin, prolactin, adrenocorticotropic hormone (ACTH), thyroid stimulating hormone (TSH), luteinizing hormone (LH), follicle stimulating hormone (FSH), human chorionic gonadotropin (HCG), motilin, interferons (alpha, beta, gamma), interluekins (IL-1 to IL-12), tumor necrosis factor (TNF), tumor necrosis factor-binding protein (TNF-bp), brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), insulin-like growth factors (IGFs), macrophage colony stimulating factor (M-CSF), granulocyte macrophage colony stimulating factor (GM-CSF), megakeratinocyte derived growth factor (MGDF), thrombopoietin, platelet-derived growth factor (PGDF), colony simulating growth factors (CSFs), bone morphogenetic protein (BMP), superoxide dismutase (SOD), tissue plasminogen activator (TPA), urokinase, streptokinase, kallikrein, blood factors such as Factor VIII and Factor IX, and polyclonal, monoclonal antibodies, chimeric antibody molecules, and antibody fragments.

In those devices intended for use as a vaccine, the active agent may be an antigen, i.e., a molecule that contains one or more epitopes that will stimulate a host's immune system to make a cellular antigen-specific immune response and/or a humoral antibody response. Thus, suitable antigens include proteins, polypeptides, antigenic protein fragments, oligosaccharides, polysaccharides, and the like. The antigen can be derived from any known virus, bacterium, parasite, plants, protozoans, or fungus, and can be a whole organism (active, split, attenuated or inactivated) or immunogenic parts thereof, e.g., cell wall components. An antigen can also be derived from a tumor. An oligonucleotide or polynucleotide that expresses an antigen, such as in DNA immunization applications, is also included in the definition of antigen. Synthetic antigens are also included in the definition of antigen, for example, haptens, polyepitopes, flanking epitopes, and other recombinant or recombinant or synthetically derived antigens (Bergmann et al (1993) *Eur. J. Immunol.* 23:2777-2781; Bergmann et al (1996) *J. Immunol.* 157:3242-3249; Suhrbier, A. (1997) *Immunol. And Cell Biol.* 75:402-408; Gardner et al (1998) 12$^{th}$ World AIDS Conference, Geneva, Switzerland (Jun. 28-Jul. 3, 1998).

C. Additives, Excipients and Pore Forming Agents

The active agent may be combined with one or more additional component, for example pharmaceutically acceptable excipient materials that can act as dispersing agents, bulking agents, binders, carriers, stabilizers, glidants, antioxidants, pH adjusters, anti-irritants, and the like. The skilled artisan will appreciate that certain excipient materials can serve several of the above-referenced functions in any particular formulation. Thus, any number of suitable excipient materials can be mixed with or incorporated into the device to provide bulking properties, alter active agent release rates, increase or impede water uptake, control pH, provide structural support, facilitate manufacturing processes and other uses known to those skilled in the art. The term "excipient" generally refers to a substantially inert material that is nontoxic and does not interact with other components of the device in a deleterious manner. The proportions in which a particular excipient may be present in the device depend upon the purpose for which the excipient is provided and the identity of the excipient.

For example, suitable carrier excipients that can also act as stabilizers for peptides include pharmaceutical grades of dextrose, sucrose, lactose, trehalose, mannitol, sorbitol, inositol, dextran, and the like. Such carriers may thus be a saccharide such as a monosaccharide, a disaccharide, a polysaccharide or a sugar alcohol. Other suitable carriers include starch, cellulose, sodium or calcium phosphates, calcium sulfate, citric acid, tartaric acid, glycine, and combinations thereof. Examples of hydrophobic excipients that can be added to the devices to slow hydration and dissolution kinetics include fatty acids and pharmaceutically acceptable salts thereof (e.g., magnesium stearate, steric acid, zinc stearate, palimitic acid, and sodium palitate).

It may also be useful to employ a charged lipid and/or detergent excipient in the devices of the present invention. Suitable charged lipids include, without limitation, phosphatidylcholines (lecithin), and the like. Detergents will typically be a nonionic, anionic, cationic or amphoteric surfactant. Examples of suitable surfactants include, for example, Tergitol® and Triton® surfactants (Union Carbide Chemicals and Plastics); polyoxyethylenesorbitans, e.g., TWEEN® surfactants (Atlas Chemical Industries); polysorbates; polyoxyethylene ethers, e.g. Brij; pharmaceutically acceptable fatty acid esters, e.g., lauryl sulfate and salts thereof; ampiphilic surfactants (glycerides, etc.); and like materials.

Other excipient materials can be added to the devices to alter porosity, for example, materials like sucrose, dextrose, sodium chloride, sorbitol, lactose, polyethylene glycol, mannitol, fructose, polyvinyl pyrrolidone or appropriate combinations thereof. Additionally, the active agents may be dispersed with oils (e.g., sesame oil, corn oil, vegetable), or a mixture thereof with a phospholipid (e.g., lecitin), or medium chain fatty acid triglycerides (e.g., Miglyol 812) to provide an oily suspension.

Still further excipeint materials that can be incorporated into the devices of the present invention include diluents of various buffer content (e.g., Tris-HCl, acetate); pH and ionic strength altering agents; additives such as antioxidants (e.g., ascorbic acid, glutathione, sodium metabisulfite); preservatives (e.g., Thimersol, benzyl alcohol, methyl paraben, propyl paraben); and dispersing agents such as water-soluble polysaccharides (e.g., mannitol, lactose, glucose, starches), hyaluronic acid, glycine, fibrin, collagen and inorganic salts (e.g., sodium chloride).

D. Devices

The polymeric devices of the present invention are in a general sense formed by the combination of an active agent with a polymer system having a hydrophobic component and a hydrophilic component, wherein the device provides for controlled release of the active agent under suitable conditions and has the physical properties as described in detail throughout the present specification. Accordingly, the term "device," as used herein, refers to a polymeric device for controlled release of an active agent of interest. The device includes a biodegradable polymer system that is either a copolymer or a polymeric blend having a hydrophobic component and a hydrophilic component, where the polymer system does not form a hydrogel when contacted with, or immersed in an aqueous system, for example when the device is implanted in a living subject. The active agent is incorporated within the polymer system such that the polymer system can provide for controlled release of the agent from the device. Optionally, one or more excipient material can also be incorporated within the polymer system in order to provide bulking properties, alter active agent release rates, increase or impede water uptake for the device, control pH, provide structural support, facilitate manufacturing processes, or like uses. When the device is administered to a subject, for example, when a device is implanted, the device releases the active agent in a controlled fashion without a lag period, or with a minimal lag period.

In the construction of devices pursuant to the present invention, the polymer system is made when a hydrophobic polymer component is co-polymerized with a hydrophilic polymer, or monomers, to yield a suitable copolymer system, most preferably a block copolymer, or when the hydrophobic polymer component is blended with a hydrophilic polymer to yield a suitable blended polymer system. The polymer system can be produced using standard copolymerization techniques, such as graft copolymerisation, polycondensation and polyaddition, optionally with an appropriate catalyst. These techniques can be carried out in conventional manner with regard to time and temperature. Alternatively, the polymer system can be produced using standard blending techniques of polymers or blending of copolymers, again carried out in conventional manner with regard to time and temperature for the procedure.

Within the polymer system itself, the hydrophobic and hydrophilic components can be present in any suitable ratio, where the specific amount of each component is selected based on the relative degree of hydrophobicity or hydrophilicity of each component, respectively, but always such that the final device product will not form a hydrogel following contact with, or immersion in an aqueous system. The resultant polymer system will thus be characterized as having a small amount of hydrophilic character, but the hydrophilic component will typically be present in the polymer system in a lesser amount relative to the hydrophobic component, not imparting hydrogel properties to the device but still producing a device that exhibits monophasic or zero-order or near zero-order release kinetics of the active agent. Accordingly, the hydrophilic component will typically be present in the polymer system in an amount of about 25 to 30 wt % or less, in some instances in an amount of about 15 wt % or less, and in some other instances in an amount of about 0.5 to 10 wt %.

In certain preferred embodiments, the polymer system is a copolymer or a polymer blend comprising greater than about 75 wt % of the hydrophobic polymer component. In other preferred embodiments the polymer system is a copolymer or a polymer blend comprising greater than about 85 wt % of the hydrophobic polymer component, and in still other embodiments, the polymer system is a copolymer or a polymer blend comprising greater than about 91 to about 98 wt % of the hydrophobic polymer component. In particular embodiments, the hydrophobic component in the polymer system is a polyhydroxy acid, such as poly(lactide), poly(glycolide), poly(lactide-co-glycolide), poly(lactic acid), poly(glycolic acid), and poly(lactic acid-co-glycolic acid), polyanhydride, polyorthoester, polyetherester, polycaprolactone, polyesteramide, polyphosphazine, polycarbonate, polyamide, or any copolymer thereof.

In a particularly preferred embodiment, the hydrophobic component of the polymer system is a poly (lactide-co-glycolide) present in the system in an amount of 90 wt % or greater.

In certain other preferred embodiments, the polymer system is a copolymer or a polymer blend comprising less than about 25 wt % of the hydrophilic polymer component. In other preferred embodiments the polymer system is a copolymer or a polymer blend comprising less than about 10 wt % of the hydrophilic polymer component. In particular embodiments, the hydrophilic component in the polymer system is a poly (alkyleneglycol), polyvinyl pyrolidone (PVP), polyvinyl alcohol (PVOH), poly (alkyleneamine), poly (alkyleneoxide), or any copolymer thereof. In preferred embodiments, the hydrophilic component in the polymer system is a poly (ethylene glycol) (PEG), and in other embodiments, the hydrophilic component is a PEG having molecular weight of between about 700 Da and about 500 kDa. In particularly preferred embodiments, the hydrophilic component is a PEG present in the polymer system in an amount of 10 wt % or less.

In one specific embodiment, the polymer system is an AB block copolymer formed from poly (DL-lactide-co-glycolide) and PEG with a molecular weight of 750, wherein the PEG is present in the polymer system at about 1.25 wt %.

Once the suitable polymer system has been selected, the copolymerization or polymer blending step can be conducted either prior to incorporation of the active agent into the polymer system, or at the same time. The active agent is thus combined with the polymer system to form the device, using standard techniques. The active agent is combined in a manner such that it will be present in the devices of the present invention in amounts ranging from about 0.1 wt % to about 80 wt % and higher, although the active agent will typically be present in an amount ranging from about 0.3 wt % to about 70 wt %, such as from about 10 wt % to 60 wt % or from about 20 wt % to about 55 wt %. The actual amount depends upon the activity of the active agent, the dose desired, the duration of release desired, the administration frequency and other variables. One skilled in the art will be able to ascertain effective amounts for selected active agents by administration and observing the desired therapeutic, pharmacological or diagnostic effect. The exact amount of the active agent in the device will thus be the amount necessary to achieve an effective concentration of the active agent in vivo, for a given period of time. This amount varies with the type of active agent used, the desired duration of the release, the target condition, desired administration frequency, the subject animal species and other factors. Preferably, the devices will contain sufficient amounts of the active agent such that release of between about 0.10 ug/kg/day and 100 mg/kg/day will yield the desired effect. These parameters will be readily appreciated by the ordinarily skilled artisan upon reading the instant specification.

Depending upon the technique used to incorporate the active agent into the polymer system and thus form the devices of the invention, the active agent may be distributed uniformly within the polymer system, or may be substantially encapsulated by the polymer system. The active agent may further be incorporated into the polymer system using an appropriate solvent system, either aqueous or non-aqueous, or the agent may be incorporated using a non-solvent process.

In addition to incorporation of the active agent within the polymer system, the devices may further include pharmaceutically acceptable excipients such as diluents, preservatives, solubilizers, emulsifiers and/or carriers needed for administration. The proportions in which a particular excipient may be present in the device depends upon the purpose for which the excipient is provided and the identity of the excipient. The optimal final pharmaceutical formulation for an active agent of interest will be determined by one skilled in the art depending upon the route of administration and desired dosage. Exemplary pharmaceutical compositions are disclosed in Remington's Pharmaceutical Sciences (1990) Mack Publishing Co., 18th Ed., Easton, Pa.

In particular embodiments of the present invention, the above-described polymer systems are used for manufacture of one or more polymeric devices for controlled release of an active agent, useful in the treatment or amelioration of the conditions the active agent is intended to treat. Thus, in one aspect of the invention, a biodegradable polymer system is used in the manufacture of a polymeric device for controlled release of an active agent, wherein the polymer system is a copolymer or a polymer blend comprising a hydrophobic component and a hydrophilic component and the polymer system does not form a hydrogel when contacted with, or immersed in an aqueous system, for example when the device is implanted in a living subject. The active agent is incorporated within the polymer system such that the polymer system provides for controlled release of the agent from the device. When the device is administered to a subject, for example, when a device is implanted, the device releases the active agent in a controlled fashion without a lag period, or with a minimal lag period. In a preferred embodiment, the polymer systems of the present invention are used for manufacture of a polymeric device for controlled release of a peptide or protein active agent. In one particularly preferred embodiment, the polymer systems are used for manufacture of a polymeric device for controlled release of a GnRH active agent, or an analogue thereof.

The devices of the present invention can be provided in any suitable form depending upon the manner in which the device will be administered. In this regard, the present devices may be administered by oral routes (e.g., as capsules such as hard capsules and soft capsules, solid preparations such as granules, tablets, pills, troches or lozenges, cachets, pellets, powders, particulates, microparticulates (and any other particulate form) and non-oral routes (e.g., as intramuscular, subcutaneous, transdermal, visceral, IV (intravenous), IP (intraperitoneal), intraarterial, intrathecal, intracapsular, intraorbital, intraocular, intratumoral, perivascular, intracranial, periophthalmic, inside the eyelid, intranasal, intrasinus, intrabladder, intravaginal, intraurethral, intrarectal, adventitial, injectable, pulmonary, inhalable, transmucosal, and other suitable forms). In preferred embodiments, the devices are administered by implantation, and are thus configured as a shaped article, such as a sphere, rod, slab, film, fiber, needle, cylinder, sheet, tube, or any other suitable geometry including microparticles, microspheres, and/or microcapsules. The devices can be provided any suitable size and shape of implantable device for specialized locations, for example as a catheter, shunt, device for continuous subarachnoid infusion, feeding tube, solid implant to prevent surgical adhesion, uterine implant, artificial sphincter, periurethral implant, splint, opthlamic implant, contact lens, plastic surgery implant, stent (containing or coated with the active agent) including an esophageal stent, gastrointestinal stent, vascular stent, biliary stent, colonic stent, pancreatic stent, ureteric stent, urethral stent, lacrimal stent, Eustachian tube stent, fallopian stent, nasal stent, sinus stent, tracheal stent, or bronchial stent, or a port including a venous access device, implanted port, epidural catheter or central catheter (PICC). The devices can be implanted at a desired site surgically, or using minimally invasive techniques employing trocars, catherers, etc. The implant can be implanted into any suitable tissue using standard techniques, such as implanted intradermally, subdermally, subcutaneously, intraperitoneally, intramuscularly, or intralumenally (e.g., intraarterially, intravenously, intravaginally, rectally, or into the periodontal space). The devices can alternatively be fabricated as part of a matrix, graft, prosthetic or coating. If an implantable device is manufactured in particulate form, e.g., as a microparticle, microsphere or microcapsule, it can then be implanted into suitable tissue using a cannula, needle and syringe or like instrument to inject a suspension of the particles.

II. Methods of Manufacture

Methods for making fibrous polymeric devices for delivery of active agents are well known in the art. See, e.g., Cowsar and Dunn, Chapter 12 "Biodegradable and Nonbiodegradable Delivery Systems" pp. 145-162; Gibson, et al., Chapter 31 "Development of a Fibrous IUD Delivery System for Estradiol/Progesterone" pp. 215-226; Dunn, et al., "Fibrous Polymers for the Delivery of Contraceptive Steroids to the Female Reproductive Tract" pp. 125-146; Dunn, et al. (1985) "Fibrous Delivery Systems for Antimicrobial Agents" from Polymeric Materials in Medication ed. C. G. Gebelein and Carraher, Plenum Publishing Corporation, pp 47-59. Any of these known methods, and numerous other methods known in the art, may be employed in the practice of the present invention in order to produce fibrous devices having the unique features described herein.

A variety of methods for processing polymers by extrusion are described in Chris Rauwendaal (1994) "Polymer Extusion" Third Revised Edition, Carl Hanser Vertag, Munich, such as plasticating extrusion, where the polymer is fed to the extruder as a solid, and melt-fed extrusion where molten polymer is fed to the extruder. As used herein, the terms "extrusion" or "melt-spinning" encompasses all these methods of manufacture. In melt-spinning, a thermoplastic polymer is heated above its melting point, extruded through an orifice, and cooled to form a filament. In one preferred embodiment for producing the devices of the present invention, a peptide active agent is mixed with the polymer prior to extrusion and the mixture is then ground to form a feedstock for re-extruding the mixture to insure uniform mixing. Although generally formed in a geometry where the cross-section is a circle, such devices can also be prepared with any other cross-sectional geometry, for example, an ellipsoid, a lobe, a square, or a triangle. The polymer can also be formed into microparticles, sheets, films or coatings, using standard processing technology.

The devices may be prepared in a variety of sizes depending on the total dose of drug and the envisioned method and site of administration. In a preferred embodiment, the device is a monolithic rod with an overall diameter between 0.05 and 5.0 mm. For subcutaneous administration in humans, an overall diameter of between 1.0 and 4.0 mm may be more preferred. The length of the device is typically between about 0.3 cm and 10 cm. For subcutaneous implantation, a more preferred length is between about 0.3 cm and 3.0 cm.

Drawing may be accomplished by passing the material around two or more sets of godets that are operated at progressively faster speeds as the material passes further down the line. The material may pass through heated ovens between the godets so that the temperature can be carefully controlled to further influence the crystallinity of the polymer. Drawing may also be used to control the final diameter of the material.

Because such structures are prepared by a continuous extrusion process, they can be provided in any length that is convenient for handling. If the formulation is sufficiently flexible, it can be wound onto a spool or into a coil and held in this way prior to cutting. Alternatively, the material can be collected as shorter lengths of perhaps a few centimeters or meters and held prior to cutting. It is also possible to cut the material to the finished device length as it is produced using a flywheel type of cutter that is situated just downstream of the die.

The amount of active agent to be incorporated and the amount used in the process will vary depending upon the particular agent, the desired effect of the active agent at the planned release levels, and the time span over which the agent should be released. Any of the above-described processes can be used to incorporate more than one active agent into the polymeric device.

III. Methods of Use

Devices produced in accordance with the invention can be administered using any suitable procedure. Depending upon the active agent to be administered, the selected form (size, shape, etc.) and the selected site of administration, the devices can be delivered or implanted using minimally invasive procedures at a site where release is desired. These procedures can include implantation using trocars or catheters, injection using standard needle and syringes (of, e.g., powders, particles, microparticles, microspheres, microcapsules), ingrafting or surgical or non-surgical placement (of, e.g., a matrix, graft, prosthetic or coating), inhalation (of, e.g., powders or particulates), and the like. The devices are designed so that the active agent is released in the desired dosage over a defined period of time. The devices are designed so that they degrade during and after release of the active agent is achieved.

In one embodiment, the device is formulated to include a GNRH molecule or GnRH analogue in a solid implant form. The device is then administered to a subject in order to target blood level, production, function, or activity of a gonadotrophin LH or FSH similar to that occurring at or near the time of greatest reproductive function in the subject, which in humans corresponds to 18 to 35 years of age. For example, a normal blood level of LH around this time is approximately 0-10.0 mIU/mL for males and approximately 0.4-92.9 mIU/mL for females (which fluctuates with reproductive cycle). A normal blood level of FSH around this time is approximately 2.0-22.6 mIU/mL for males and approximately 2.9-29.5 mIU/mL for females (which also fluctuates with reproductive cycle). Administration of the GnRH or GNRH analogue implant is suitable to alter the blood level, production, function, or activity of a gonadotrophin LH or FSH to acheive the desired level(s).

In another embodiment, the device is formulated to include a GnRH molecule or GnRH analogue in a solid implant form. The device is then administered to a subject in order to the target blood level, production, function, or activity of LH or FSH to levels that are undetectable or nearly undetectable. For example, a blood level of 0.7 mIU/mL for both LH and FSH is currently undetectable in a clinical laboratory.

In another embodiment of the invention, the device is formulated to include a GNRH molecule or GnRH analogue in a solid implant form. The device is then administered to a subject in order to the target blood level, production, function, or activity of LH or FSH to levels as low as possible without unacceptable adverse side effects. An unacceptable adverse side effect is an adverse side effect that, in the reasonable judgment of one of ordinary skill in the art, has costs that outweigh the benefits of treatment.

In the practice of these and other related methods, the subject's blood level, production, function, or activity of LH or FSH may be periodically monitored and the combinations, quantities, and dosage regimens of the LH/FSH-inhibiting agents may be titrated or varied in order to achieve the target blood level, target production, target function or target activity of LH and FSH. In a particularly preferred embodiment, the dosage for an GnRH analogue, for example leuprolide acetate, may be between approximately 0.01 mcg/kg/hour and approximately 100 mg/kg/day, or other schedules that will be apparent to one of ordinary skill in the art, in light of this specification. In these methods, the subject may initially be administered a low dose, for example approximately 0.01 mcg/kg/hour. After approximately two weeks, LH and FSH blood levels may be measured. If LH and FSH bloods levels are still higher than the target, then the dose may be increased (for example by 0.1 mcg/kg/hour). This titration can be repeated until the blood level, production, function or activity of LH or FSH reaches the desired target blood level, production, function, or activity for LH or FSH, as set forth above.

For example, a 30 mg time-released dose of leuprolide acetate can be administered to an adult male subject. The leuprolide acetate active agent is provided in a biodegradable polymer system to supply a polymeric device for controlled release of the active agent. The polymer system is a copolymer or a polymer blend comprising a hydrophobic component and a hydrophilic component and the polymer system does not form a hydrogel when contacted with, or immersed in an aqueous system, for example when the device is implanted in the subject. The leuprolide acetate active agent is incorporated within the polymer system such that the polymer system provides for controlled release of the agent from the device. When the device is administered to the subject, for example, when it is implanted, the device releases the active agent in a controlled fashion without a lag period, or with a minimal lag period. In this manner, the leuprolide can be gradually released over a period of several months. After a period of two weeks, the subject's blood level of LH may be undetectable and the subject's blood level of FSH may be approximately 5 mIU/mL.

In another example, a dose of 1.88 mg time-released dose of leuprolide acetate can be administered to a subject. The leuprolide acetate active agent is provided in a biodegradable polymer system to supply a polymeric device for controlled release of the active agent. The polymer system is a copolymer or a polymer blend comprising a hydrophobic component and a hydrophilic component and the polymer system does not form a hydrogel when contacted with, or immersed in an aqueous system, for example when the device is implanted in the subject. The leuprolide acetate active agent is incorporated within the polymer system such that the polymer system provides for controlled release of the agent from the device. When the device is administered to the subject, for example, when it is implanted, the device releases the active agent in a controlled fashion without a lag period, or with a minimal lag period. In this manner, the leuprolide can be gradually released over approximately one month, and is expected to reduce LH and FSH blood levels to undetectable levels in the subject. It will be apparent to one of ordinary skill in the art, in light of this specification, that in order to achieve this target, the dosage of the leuprolide active agent will vary from subject to subject in light of factors such as age, gender, body weight, diet, the disease being treated, the progression of the disease, and other drugs being administered.

Below are examples of specific embodiments for carrying out the present invention. The examples are offered for illustrative purposes only, and are not intended to limit the scope of the present invention in any way

EXAMPLE 1

Poly (DL-Lactide-Co-Glycolide) Peg Block Copolymer Implant

Methods

A 90:10 poly (DL-lactide-co-glycolide) PEG block copolymer was prepared using 8.3 wt % of a monomethoxy terminated poly (ethylene glycol) having a molecular weight of 5,000 [mPEG-5000] as initiator with DL-lactide-co-glycolide to produce a block copolymer having an inherent viscosity of 0.89 dL/g in $CHCl_3$ at 30° C. The resulting copolymer was then melt extruded to produce rods of about 1.5 mm diameter and the rods were cut into devices of about 2 cm length. The devices were then placed into clean scintillation vials containing 10 mL of 67 mM Sorenson's phosphate buffer. The samples were stored in a 37° C. incubator. Complete buffer exchanges were done following 1, 2, 4, 6, 8, 10, 12, 14, and 16 weeks of exposure. At each of the above sample periods, three devices were removed from the study, and the wet weight was recorded. The devices were dried (ambient pressure and RT followed by vacuum drying at less than 18 mm Hg), and the dry weight of each device was recorded.

Results

The water uptake of the polymer is shown in FIG. 1. The results show that the devices absorb water to a greater degree in that the diameter increases.

EXAMPLE 2

Release Properties of Leuprolide Acetate Containing Implants

Materials

Nine parts of leuprolide acetate milled to a mean particle size of between 3 and 10 microns and 27 parts of mPEG 750 initiated 90:10 poly (DL-lactide-co-glycolide) [mPEG-750/(90:10 □L-PLG)] having an inherent viscosity of 0.89 dL/g in $CHCl_3$, an mPEG content of 1.25 wt %, and having been ground to pass through a 1 mm screen, were combined and thoroughly mixed. The powder blend was then compounded by melt extrusion on a 0.375-inch diameter screw extruder at temperatures of 80 to 120° C. The extrudate is ground and re-extruded on the same equipment and within the same temperature range to produce a rod having a diameter of about 1.5 mm diameter. The rod was then cut to form devices of about 2 cm length.

The devices were tested in vitro by placing individual devices in 10 mL of 67 mM Sörensen's phosphate buffer (pH 7.4) containing 0.05 wt % sodium azide and incubated at 37° C. Periodically, the buffer was exchanged for fresh buffer, and the old buffer was assayed to determine the amount of leuprolide that has been released from the implants.

Results

FIG. 2 shows that the release from the devices shows a burst over a period of about 7 days followed by a slower constant release of leuprolide.

EXAMPLE 3

Release Properties of Leuprolide acetate containing Implants

The experiment of Example 2 was repeated using an mPEG-5000/(90:10 DL-PLG) having an IV=0.89 dL/g and containing 8.3 wt % mPEG. A similar release profile was observed as is shown in FIG. 3.

Modifications and variations of the present invention will be obvious to those skilled in the art and are intended to come within the scope of the appended claims.

What is claimed is:

1. A polymeric device for controlled release of an active agent of interest, said device comprising
a biodegradable polymer system, wherein the polymer system comprises an AB copolymer comprising a hydrophobic A component and a hydrophilic B component, wherein the A component comprises a copolymer of lactide, glycolide or caprolactone, and the B component comprises a polyalkyleneglycol; and
an active agent, wherein the hydrophilic component is present in the polymer system in an amount up to 30 wt %, and wherein the polymer system does not form a hydrogel when the device is contacted with an aqueous system.

2. The device of claim 1 wherein the agent is present in an amount up to 40 wt %.

3. The device of claim 1 or 2, wherein the active agent is a peptide.

4. The device of claim 3, wherein the peptide is a therapeutic and/or prophylactic peptide selected from the group consisting of hormones, growth factors, neuroactive agents, melanotropic peptides, cell adhesion factors, cytokines, and biological response modifiers.

5. The device of claim 4, wherein the peptide is a GnRH molecule or a GnRH analog.

6. The device of claim 5, wherein the GnRH analog is selected from the group consisting of desorelin, tryptorelin, goserelin, and leuprolide.

7. The device of claim 1, wherein the hydrophilic component is present in an amount of up to 25 wt %.

8. The device of claim 1, wherein the hydrophilic component is present in an amount of up to 15 wt %.

9. The device of claim 1, wherein the hydrophilic component is present in an amount of between 0.5 and 10 wt %.

10. The device of claim 1, wherein the B component comprises a polyalkyleneglycol at 1.25 wt % and the A component comprises poly (lactide-co-glycolide).

11. The device of claim 1, wherein the active agent is distributed uniformly within the polymer system.

12. The device of claim 1, wherein the active agent is incorporated using a non-solvent process.

13. The device of claim 1, wherein the device is formed by dry melt extrusion.

14. The device of claim 1, wherein the device is formed by melt extrusion of the copolymer mixed with peptide.

15. The device of claim 1, wherein the active agent is released with linear release kinetics.

16. The device of claim 1, wherein the polymer system comprises greater than 75 wt % of the hydrophobic component.

17. The device of claim 16, wherein the polymer system comprises greater than 85 wt % of the hydrophobic component.

18. The device of claim 17, wherein the polymer system comprises greater than 91 wt % of the hydrophobic component.

19. The device of claim 18, wherein the polymer system comprises greater than 98 wt % of the hydrophobic component.

20. The device of claim 1, wherein the hydrophilic component of the polymer system comprises polyethylene glycol.

21. The device of claim 1 provided in the form of a fiber, needle or rod.

22. The device of claim 1 provided in the form of a sheet, film or coating.

23. The device of claim 1 provided in microparticulate form.

24. The device of claim 1 free of solvent residue.

25. The device of claim 1 for treating disease wherein the active agent is a GnRH molecule or a GnRH analogue.

26. The device of claim 1, wherein the active agent is a GnRH molecule or a GnRH analogue used for lowering gonadotropin levels.

27. A method of making the device of claim 1, said method comprising mixing the polymer system and the active agent, extruding the mixture of the polymer system and active agent, grinding or milling the extruded mixture, and feeding the ground or milled extruded mixture into an extruder.

28. A method of making a polymeric device for the controlled release of an active agent of interest, said method comprising combining a biodegradable polymer system with the active agent to form the device, wherein the polymer system comprises an AB copolymer comprising a hydrophobic A component and a hydrophilic B component, the A component comprising a copolymer of lactide, glycolide or caprolactone, and the B component comprising a polyalkyleneglycol, and wherein the hydrophilic component is present in the polymer system in an amount up to 30 wt %, and wherein the polymer system does not form a hydrogel when the device is contacted with an aqueous system.

29. The method of claim 28 wherein the agent is present in an amount up to 40 wt %.

30. The method of claim 28 or 29, wherein the active agent is a peptide.

31. The method of claim 30, wherein the peptide is a therapeutic and/or prophylactic peptide selected from the group consisting of hormones, growth factors, neuroactive agents, melanotropic peptides, cell adhesion factors, cytokines, and biological response modifiers.

32. The method of claim 31, wherein the peptide is a GnRH molecule or a GnRH analog.

33. The method of claim 32, wherein the GnRH analog is selected from the group consisting of desorelin, tryptorelin, goserelin, and leuprolide.

34. The method of claim 28, wherein the hydrophilic component is present in an amount of up to 25 wt %.

35. The method of claim 28, wherein the hydrophilic component is present in an amount of up to 15 wt %.

36. The method of claim 28, wherein the hydrophilic component is present in an amount of between 0.5 and 10 wt %.

37. The method of claim 28, wherein the B component comprises a polyalkyleneglycol at 1.25 wt % and the A component comprises poly(lactide-co-glycolide).

38. The method of claim 28, wherein the active agent is distributed uniformly within the polymer system.

39. The method of claim 28, wherein the active agent is released with linear release kinetics.

40. The method of claim 28, wherein the polymer system comprises greater than 75 wt % of the hydrophobic component.

41. The method of claim 40, wherein the polymer system comprises greater than 85 wt % of the hydrophobic component.

42. The method of claim 41, wherein the polymer system comprises greater than 91 wt % of the hydrophobic component.

43. The method of claim 42, wherein the polymer system comprises greater than 98 wt % of the hydrophobic component.

44. The method of claim 28, wherein the hydrophilic component of the polymer system comprises polyethylene glycol.

45. The method of claim 28, further comprising providing the device in the form of a fiber, needle or rod.

46. The method of claim 28, further comprising providing the device in the form of a sheet, film or coating.

47. The method of claim 28, further comprising providing the device in microparticulate form.

48. The method of claim 28, wherein the device is free of solvent residue.

49. The device of claim 1, wherein the device provides for monophasic release of the active agent.

50. The method of claim 28, wherein the device provides for monophasic release of the active agent.

\* \* \* \* \*